United States Patent

Roggero et al.

[11] 3,989,642
[45] Nov. 2, 1976

[54] POLYMERIZATION CATALYST

[75] Inventors: Arnaldo Roggero; Alessandro Mazzei; Antonio Proni, all of San Donato Milanese, Italy

[73] Assignee: Snam Progetti S.p.A., San Donato, Milanese, Italy

[22] Filed: Sept. 24, 1975

[21] Appl. No.: 616,245

Related U.S. Application Data

[63] Continuation-in-part of Ser. No. 339,939, March 9, 1973, abandoned.

[30] Foreign Application Priority Data

Mar. 11, 1972 Italy .................................. 21728/72

[52] U.S. Cl. ..................... 252/431 N; 252/431 R; 252/431 L
[51] Int. Cl.² ..................... C08F 4/46; C08F 4/48; C08F 4/50; C08F 4/52
[58] Field of Search ......... 252/431 N, 431 R, 431 L

[56] References Cited
UNITED STATES PATENTS

| | | | |
|---|---|---|---|
| 3,026,311 | 3/1962 | Coover et al. | 252/431 R X |
| 3,609,101 | 9/1971 | Niemann | 252/431 L |
| 3,629,160 | 12/1971 | Tushaus | 252/431 N X |

FOREIGN PATENTS OR APPLICATIONS

| | | | |
|---|---|---|---|
| 749,942 | 1/1967 | Canada | 252/431 R |

*Primary Examiner*—Patrick P. Garvin
*Attorney, Agent, or Firm*—Ralph M. Watson

[57] ABSTRACT

A new catalyst, useful in the homo-, co- and ter-polymerization of monomers of the episulphide, vinylic, lactonic, dimethylketene and aldehyde type, is prepared by reacting a metal selected from groups IA, IIA or IIIA of the periodic system, or a hydride, alkyl or amino derivative thereof (e.g. LiBut) with a compound (e.g.

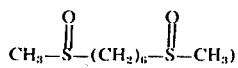

containing at least two groups selected from SO and $SO_2$ and constituted by one or more repeating units represented by the formula:

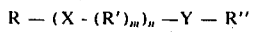

wherein, X and Y, which may be the same or different are chosen from SO and $SO_2$; R and R'' are chosen from methyl, alkyl containing 2–10 C atoms, cycloalkyl, aryl, aralkyl, alkylcycloalkyl and bivalent radicals adapted to react together to form a closed ring: R' is chosen from arylenic, cycloalkylenic, alkyl-arylenic, alkyl-cycloalkylenic bivalent radical and a methylenic chain containing from 1 to 20 C atoms; $m$ is 0 or 1; and $n$ is 1, 2 or 3.

4 Claims, No Drawings

POLYMERIZATION CATALYST

This is a continuation-in-part of Ser. No. 339,939, filed Mar. 9, 1973, now abandoned.

The present invention relates to new polymerization catalysts, to the process for their preparation, and to the polymerization process which makes use of said catalysts.

It is known, from previous patents owned by the assignee of this application, that it is possible to obtain active catalytic systems for the polymerization of epi-sulphides by reacting suitable compounds with mono-sulphoxides or monosulphones. We have now found that the presence of two or more SO or $SO_2$ groups in the same molecule provides more active catalytic systems and polymers having a higher molecular weight.

This is probably due to the fact that in the same molecule there are present several active centres.

Hence, it provides also the possibility of utilizing these catalysts in the block copolymerization of two monomers A and B to give products of the type A-B-A.

Said catalysts are obtained by reaction of a metal or its hydride, alkyl or amido derivatives, with compounds which contain two or more SO and $SO_2$ groups. The metal is chosen from the ones belonging to groups IA, IIA and IIIA of the periodic system of the elements, according to "Handbook of Chemistry and Physics" published by Chemical Rubber Publishing Co. (39th edition). Whereas the compounds containing at least two of groups SO and $SO_2$ are chosen from those derivatives containing in their molecule one or more repeating units of the type:

$$R - (X - (R')m)_n - Y - R'' \qquad (1)$$

wherein X and Y, equal or different, are groups chosen from SO and $SO_2$; R and R'' may be methyl, alkyl groups containing from two to 10 atoms of carbon, cycloalkyl, aryl, aralkyl, alkylcycloalkyl groups, or may be bivalent radicals able to react together in such a way as to form a cloud ring; R' represents an arylenic, cycloalkylenic, alkyl-arylenic, alkyl-cycloalkylenic bivalent radical or a methylenic chain containing from 1 to 20 carbon atoms; $m$ is chosen from 0 and 1 whereas $n$ is an integer which may be 1, 2 or 3.

Examples of metals or their derivatives particularly suitable for use in the practice of the invention are Li, Na, K, LiH, $CaH_2$, NaH, $ZnH_2$, LiR, $ZnR_2$, $MgR_2$, $AlH_3B$, $AlR_3$, $LiNH_2$, $Mg(NH_2)_2$ and so on where B is a Lewis base.

We may cite as examples of compounds corresponding to the formula (1) the following:

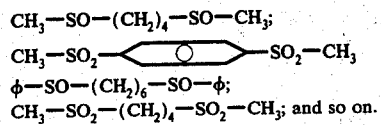

$CH_3-SO_2-\phantom{x}\phantom{x}\phantom{x}-SO_2-CH_3$ $\phi-SO-(CH_2)_6-SO-\phi$;

$CH_3-SO_2-(CH_2)_4-SO_2-CH_3$; and so on.

The catalyst of the invention is prepared by reacting the above-mentioned compounds in different ratios (metallating agent/disulphoxide or disulphone or polyderivative) between 10 and 0.3 and preferably in a ratio of 1:1 between metallating agent and SO and/or $SO_2$ group in a suitable solvent and in the temperature range between $-80°$ and $+80°$ C.

The reaction solvent may be chosen from the aliphatic and aromatic hydrocarbons, tetrahydrofuran, dioxane, hexamethyl phosphoramide, liquid ammonia and others.

The catalysts obtained as described above are used in polymerization processes which are effected in polar solvents or in mixtures of them, at temperatures in the range $-40° - +100°$ C and preferably between $-20° - +40°$ C.

The concentration of the catalyst is between 0.001% and 5% as to the charged moles of monomer or monomers, and preferably between 0.01% and 1%.

The monomers which may be polymerized according to the polymerization process making use of the catalysts of the invention, may be chosen from a wide range of compounds. Particular advantages have been observed by making use of the monomers belonging to one of the following classes:

1. Episulphides among the which may be cited in particular: ethylene sulphide, propylene sulphide, isobutene-episulphide, styrene-episulphide, vinyl-cyclohexene episulphide, allyloxy-2-3 epithiopropane, butadiene mono-episulphide and so on.
2. Monomers of the vinylic type, as for example: acrylonitrile, methacrylonitrile, methylmethacrylate, styrene, methylvinylketone, acrylamide and so.
3. Monomers of the lactone type.
4. Monomers of the dimethylketene or of the aldehyde type.

According to the polymerization process of the present invention homopolymers, copolymers and terpolymers of the cited monomers may be obtained.

Results of particular interest have been obtained in the formation of:

a. homopolymers of the cited monomers;
b. statistical and block copolymers of episulphide monomers;
c. terpolymers of episulphide monomers;
d. statistical and block copolymers of vinylic and episulphide monomers;
e. copolymers of vinylic monomers;
f. statistical and block copolymers of episulphide and lactonic monomers.

The afore-mentioned and other operational characteristics will become more evident from a consideration of the examples which are given hereinafter.

EXAMPLE 1

Preparation of

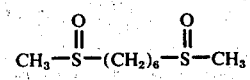

and of the corresponding reaction product with Li-butyl (catalyst A) - In a three necks flask equipped with stirrer, dropping funnel and thermometer, 4.06 gr. of NaH equal to 170 mmoles in a stream of argon are placed 100 cc of dimethyl sulphoxide are dropped slowly and under stirring. The whole is kept under stirring for 6 hours at $+40°$ C, then is filtered and titrated. The reaction mixture containing 95 mmoles of

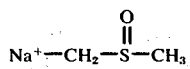

is allowed to react with 48 mmoles of Br—CH$_2$—CH$_2$—CH$_2$—CH$_2$—Br diluted with 10 cc of DMSO. The reaction is weakly exothermic The reaction is maintained for 8 hours at 60° C; DMSO is removed by vacuum distillation; ether is added and then the whole is filtered and cold washed with 50 cc of THF.

Extraction of the solid in a Kumagawa extractor with hot THF is effected, the extract in tetrahydrofuran is precipitated with anhydrous ether, then is filtered and dried, thus obtaining 5.6 gr. of

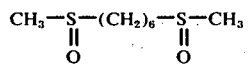

(yield = 56%). In a 250 cc three necks flask, previously deaerated and in argon atmosphere, equipped with a cooler, dropping funnel and thermometer, 4.1 gr. (19.4 mmoles) of

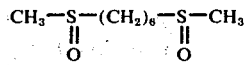

are placed; then 200 cc of anhydrous dioxane are added (dehydration of the dioxane on LiAlH$_4$).

Heating to 40°–50° C until complete dissolution is effected, 40 mmoles of Li-butyl in hexane solution are added slowly.

There is a noticeable development of gas and the temperature rises up to +55° C. About the end of the reaction the formation of a white precipitate is observed. It is kept under stirring for 3 hours at 50° C. The reaction mixture is filtered, is washed repeatedly with warm THF in order to eliminate the excess of Li-butyl and the possible unreacted product and it is dried under a vacuum for 1-2 hours. The so dried product is dissolved in HMPA (hexamethyl-phosphoramide).

| Characterization: | | | | |
|---|---|---|---|---|
| a) elementary analysis | C % | H % | S % | Li % |
| theoretical | 43.2 | 7.2 | 28.8 | 6.4 |
| found value | 42 | 7.5 | 28.1 | 6.4 |
| b) with C$_2$H$_5$Br. | | | | |

In a 100 cc three necks flask previously deaerated and under argon atmosphere, equipped with stirrer, dropping funnel and thermometer, 0.2 gr. of catalyst A (0.90 mmoles) are placed and 0.50 cc of THF are added in order to obtain a white suspension.

6 mmoles of C$_2$H$_5$Br are added and the stirring continues for 16 hours at 30° C.

There is obtained a clear solution which is evaporated to dryness to give a white hygroscopic solid, which analyzed by mass spectroscopy presents a MW 266 corresponding to the sum of two C$_2$H$_5$ groups with catalyst A.

EXAMPLE 2

Reaction of

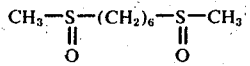

with NaNH$_2$ (catalyst B). In a flask equipped with a tight glass stirrer of the Quickfit type and with a charging funnel with jacket are placed 0.39 gr. of NaNH$_2$ equal to 10 mmoles and these are solubilized with 40 cc of liquid NH$_3$ at −70° C. 5 mmoles of

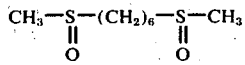

suspended in 40 cc of THF are added. The stirring is kept for 10 hours at −45° C NH$_3$ is removed and the dried solid content is used in the polymerization.

A characterization with BrEt is effected on a portion of this with the same procedure as Example 1.

The obtained product analyzed by mass spectroscopy is in agreement with a structure that is similar to the preceding one.

EXAMPLE 3

Reaction between MgEt$_2$ and

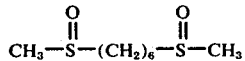

(catalyst C). In a flask equipped with magnetic stirrer, dropping funnel and cooler are placed 0.5 gr. of

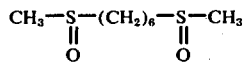

equal to 2.4 mmoles and these are dissolved in 70 cc of THF at +40° C. Afterwards 4.8 mmoles of MgEt$_2$ in 20 cc of tetrahydrofuran solution are added. The formation of a precipitate and the contemporaneous development of gas, which disappears after 30' ageing, is observed.

The temperature of +40° C is maintained for 18 hours; the opalescent solution is concentrated and precipitated with hexane; it is filtered, washed with THF (tetrahydrofuran) and hexane to remove the unreacted products, it is dried and the precipitate (ppt) is used in polymerization.

EXAMPLE 4

Reaction between Zn(C$_2$H$_5$)$_2$ and

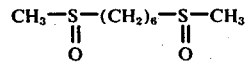

(catalyst D).

According to the procedure of Example 3, 0.75 mmoles of

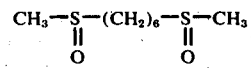

are reacted with 0.75 mmoles of ZnEt$_2$ in THF. Development of gas is observed and the solution becomes opalescent. The temperature is maintained at +50° C for 16 hours, the solution is concentrated and precipitated with hexane, washed with THF and hexane, dried and the precipitate is used in polymerization.

EXAMPLE 5

Reaction between AlH$_3$N(CH$_3$)$_3$ and

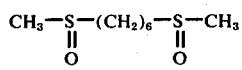

(catalyst E).

By following the procedure described in the preceding Example, 0.57 mmoles of

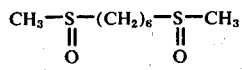

are reacted with 0.57 mmoles of AlH$_3$N(CH$_3$)$_3$ in 40 cc of toluene. The temperature of 60° C is maintained for 1 hour, the precipitate is filtered, washed with THF and toluene, it is dried and used in polymerization.

EXAMPLE 6

Preparation of CH$_3$—SO$_2$—(CH$_2$)$_6$—SO$_2$—CH$_3$ and reaction with Li But (catalyst F).

In a 3 necked flask equipped with stirrer, dropping funnel and cooler 1 gr. (4.7 mmoles) of

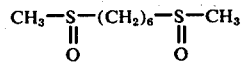

is placed and it is dissolved in the least possible amount of glacial acetic acid. It is heated to 70° C and the necessary amount of H$_2$O$_2$ is added drop by drop. The reaction is maintained at 70° C for 10 hours and subsequently is let stand for a night. A white precipitate is formed, which is crystallized by alcohol. The product is dried carefully under vacuum. 1.05 gr. of the desired product (R=87%) are obtained. According to the procedures described in Example 1, 1.05 gr. (4.1 mmoles) of CH$_3$—SO$_2$—(CH$_2$)$_6$—SO$_2$—CH$_3$ are reacted with 8.2 mmoles of Li But. The product is dried and dissolved in HMPA.

Characterizations:
a) elementary analysis

| | C % | H % | S % | Li % |
|---|---|---|---|---|
| theoretical | 37.8 | 6.3 | 25.2 | 5.5 |
| found | 37.5 | 6.0 | | 5.7 |

Characterizations:
b) with BrEt.

The reaction has been described in detail in Example 1.

The mass spectroscopy analysis is in agreement with that of a compound having a MW = 298.

EXAMPLE 7

Preparation of

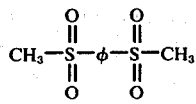

and reaction with Li But (catalyst G). The CH$_3$—S—$\phi$—S—CH$_3$ is prepared as described in Ber. 1909 42 p. 2721–2731.

On that product, oxidation under controlled conditions with H$_2$O$_2$ in CH$_3$COOOH is effected obtaining as reaction product a white solid crystallized by pure alcohol with melting point of 188° C, whose analysis with mass spectroscopy-nuclear magnetic resonance discloses the compound

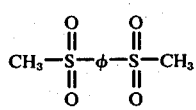

According to the procedure previously described in Example 1, 1.5 gr. (8.4 mmoles) of

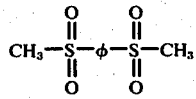

are reacted with 17 mmoles of Li But.

The product is dried, dissolved in hexamethyl phosphoramide and used in polymerization.

EXAMPLES 8–13

The polymerization tests are carried out in a 250 cc vessel, previously deaerated and under argon; firstly the catalyst of Example 1 with the solvent is charged and then the monomer. The tests are performed at 30° C in a thermostatically controlled bath. The relevant data are shown in Table 1.

TABLE 1

| Test Nr. | Monomer Type | Amount | | Cat. A Amount | | Solvent Type | Amount | | Conver. % | [η] dl/g | |
|---|---|---|---|---|---|---|---|---|---|---|---|
| 8 | Ethylene sulphide | 60 | mmoles | 0.03 | mmoles | HMPA | 25 | cc. | 100 | n.a. | |
| 9 | Propylene sulphide | 63 | " | 0.05 | " | HMPA-THF | 5–20 | cc. | 100 | 2.24 tol. | 30° C |
| 10 | Acrylonitrile | 63 | " | 0.1 | " | HMPA | 25 | " | 84 | 0.29 DMFA | " |
| 11 | Methylmethacrylate | 100 | " | 0.08 | " | HMPA | 30 | " | 40 | 1.39 tol. | " |
| 12 | Methacrylonitrile | 63 | " | 0.07 | " | HMPA | 25 | " | 93 | n.a. | |
| 13 | Pivalolactone | 63 | " | 0.07 | " | HMPA | 25 | " | 95 | n.a. | |

HMPA = hexamethylphosphoramide
THF = tetrahydrofuran
DMFA = dimethylformamide

EXAMPLE 14

With the procedures previously described, 0.05 mmoles of the reaction product of

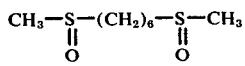

with NaNH₂ (named catalyst B) in 25 cc of THF are charged in a deaerated vessel and under argon.

Subsequently 63 mmoles of propylene sulphide are added.

The test is effected in a thermostatically controlled bath at 30° C. 4.65 gr. of polymer (yield 100%) with a [η] toluene at 30° C of 2.10 dl/g are obtained.

EXAMPLE 15

By making use of the usual procedures in a deaerated vessel and under argon are charged 0.05 mmoles of catalyst prepared by CH₃—SO₂—(CH₂)₆—SO₂—CH₃ with Li But (named catalyst F) in 25 cc of solvent (5 of HMPA + 20 THF). 63 mmoles of propylenesulphide are added. The test is effected in thermostatically controlled bath at 30° C.

4.65 gr. of polymer (yield 100%) are obtained, with a [η] = 1.84 dl/g at 30° C in toluene.

EXAMPLE 16

By making use of the procedures described mg. 25 of the reaction product between MgEt and

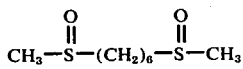

(named catalyst C) are charged in a deaerated vessel and under argon, then they are dissolved in 30 cc of HMPA and 63 mmoles of propylene sulphide are added. The polymerization is effected at 30° C by obtaining gr. 4.4 of polymer (yield 98%) with a [η] = 1.32 dl/g in toluene at 30° C.

EXAMPLE 17

By making use of the previously described procedures, in a deaerated vessel and under argon are charged 0.05 mmoles of the precipitate obtained by reacting Zn(C₂H₅)₂ and

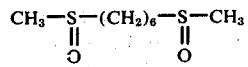

(named catalyst D); then they are dissolved in HMPA and 76 mmoles of propylenesulphide are added. The polymerization is carried out at 30° C 3.4 gr. of polymer (yield 61%) are obtained with a [η] = 1.86 dl/g in toluene at 30° C.

EXAMPLE 18

By making use of the previously described procedures, 0.05 mmoles of product obtained from the reaction between AlH₃N(CH₃) and

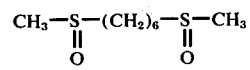

(named catalyst E) are charged in a deaerated vessel and under argon. Then they are suspended with 20 cc of HMPA and 57 mmoles of propylene sulphide are added. The polymerization is carried out at 30° C, obtaining gr. 3 of polymer (yield 70%) with a [η] = 1.80 dl/g in toluene at 30° C.

EXAMPLE 19

By making use of the previously described procedures 0.05 mmoles of product obtained by the reaction of

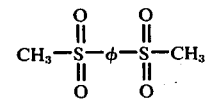

with Li But. (named catalyst G) are charged in a deaerated vessel and under argon. They are dissolved in HMPA and 63 mmoles of propylene sulphide are added. The polymerization is carried out at 30° C, by obtaining gr. 3.2 of polymer (yield 70%) with a [η] = 1.79 dl/g at 30° of toluene.

EXAMPLES 20–26

The copolymerization and terpolymerization tests have been carried out in a 250 cc vessel, previously deaerated, under argon. First the catalyst A with the solvent is charged and then the mixture of monomers. The tests are maintained at 30° C by a thermostatically controlled bath. The data are shown in Table 2.

TABLE 2

| | Monomer | | Comonomer | | Termonomer | |
|---|---|---|---|---|---|---|
| | Type | Amount | Type | Amount | Type | Amount |
| 20 | Propylen sulphide | 45 mmoles | Ethylenesulphide | 19 mmoles | | |
| 21 | Propylen sulphide | 63 mmoles | Acrylonitrile | 10 mmoles | | |
| 22 | Propylen sulphide | 63 mmoles | Allyltiranylether | 3.15 " | | |
| 23 | Propylen sulphide | 63 mmoles | Ethylenesulphide | 24 " | Allyltiranylether | 6.14 mmoles |
| 24 | Propylen sulphide | 76 mmoles | Metacrylonitrile | 11 " | | |
| 25 | Propylen sulphide | 67 mmoles | Acrylonitrile | 33 " | Allyltiranylether | 4 " |
| 26 | Acrylonitrile | 50 mmoles | Methylmethacrylate | 50 " | | |

| | Cat. A Amount | | Solvent | | Composition | |
|---|---|---|---|---|---|---|
| 20 | 0.0128 | mmoles | HMPA 20cc | propylensulphide | 80 % -Ethylensulphide | 20 % |
| 21 | 0.015 | " | DMSO 20cc | " | 75 % -Acrylonitrile | 25 % |
| 22 | 0.033 | " | DMSO 20cc | " | 95 % -Allyltiranylether | 5 % |
| 23 | 0.015 | " | HMPA 20cc | " | 60 % -Ethylensulphide | 33 % ATE 7 % |
| 24 | 0.037 | " | DMSO 25cc | " | 83 % -Metacrylonitrile | 17 % |
| 25 | 0.25 | " | DMSO 40cc | " | 74 % -ACRYLONITRILE | 19 % ATE 6 % |

TABLE 2-continued

| 26 | 0.1 | " | HMPA 25cc | acrylonitrile | 60 % | -Methylmethacrylate | 40 % |

| | [η] dl/g | | Conversion % |
|---|---|---|---|
| 20 | 1.89 toluene | 30° C | 98 |
| 21 | 2.17 CHCl₃ | 30° C | 100 |
| 22 | 2.20 toluene | 30° C | 100 |
| 23 | 1.15 toluene | 30° C | 97 |
| 24 | 0.46 DMFA | 30° C | 65 |
| 25 | 0.7 CHCl₃ | 30° C | 76 |
| 26 | n.a. | | 70 |

DMSO = dimethylsulphoxide
DMFA = dimethylformamide
ATE = allyltiramylether

Herewith are reported the technological features of the polymers prepared according to the examples 22 – 23 – 25, after vulcanization, by making use of the following recipe:

| Polymer | 100 parts |
|---|---|
| Antioxidizer 2246 | 1 part |
| Stearic acid | 1 part |
| HAF | 50 parts |
| ZnO | 5 parts |
| MBT | 0.5 parts |
| TMDT | 1 part |
| Sulphur | 2 parts |

HAF = high abrasion furnace
MBT = mercaptobenzothiazole
TMDT = tetramethylthiuramedisulphide The vulcanization has been carried out at 145° C.

EXAMPLE 22

| Minutes | Modulus 100 % | Kg/cm² 200 % | 300 % | T.S. Kg/cm² | E. % | p.set % |
|---|---|---|---|---|---|---|
| 7 | 34 | 69 | 103 | 147 | 505 | 20 |
| 15 | 52 | 112 | — | 142 | 260 | 8 |
| 30 | 58 | 124 | — | 124 | 205 | 4 |
| 45 | 61 | — | — | 121 | 190 | 2 |
| 60 | 59 | — | — | 114 | 180 | 2 |

EXAMPLE 23

| Minutes | Modulus 100 % | 200 % | 300 % | Kg/cm² | E. % | p.set % |
|---|---|---|---|---|---|---|
| 15 | 51 | 132 | — | 145 | 235 | 4 |

-continued

| Minutes | Modulus 100 % | Kg/cm² 200 % | 300 % | T.S. Kg/cm² | E. % | p.set % |
|---|---|---|---|---|---|---|
| 30 | 62 | — | — | 125 | 175 | 0 |
| 45 | 66 | — | — | 118 | 160 | 0 |
| 60 | 72 | — | — | 111 | 145 | 0 |

EXAMPLE 25

| Minutes | Modulus 100 % | Kg/cm² 200 % | 300 % | T.S. Kg/cm² | E. % | p.set % |
|---|---|---|---|---|---|---|
| 7 | 19 | 32 | 41 | 48 | 445 | 8 |
| 15 | 51 | 96 | — | 115 | 285 | 6 |
| 30 | 63 | — | — | 119 | 195 | 4 |
| 45 | 55 | 101 | — | 128 | 295 | 6 |
| 60 | 66 | — | — | 100 | 160 | 0 |

EXAMPLES 27–30

The polymerization tests to obtain block copolymers have been carried out in a 250 cc reactor, previously deaerated and under argon.

First catalyst (A) with the solvent is charged and then the monomer 1. Once the polymerization of the 1st monomer is finished, after 5–8 hours, the obtained polymer is dissolved in 50 cc of THF and the 2nd monomer is added, carrying the reaction to completion at the temperature of 30° C. The data are shown in Table 3.

TABLE 3

| | Monomer 1 | | Monomer 2 | | Cat. | |
|---|---|---|---|---|---|---|
| | Type | Amount | Type | Amount | Type A | Solvent |
| 27 | Propylensulphide | 63 mmoles | Ethylensulphide | 40 mmoles | 0.064 mmoles | HMPA 20 cc |
| 28 | Propylensulphide | 63 mmoles | Acrylonitrile | 35 mmoles | 0.04 mmoles | HMPA 20 cc |
| 29 | Propylensulphide | 63 mmoles | Metacrylonitrile | 10 mmoles | 0.015 mmoles | HMPA 20 cc |
| 30 | Propylensulphide | 63 mmoles | Pivalolactone | 10 mmoles | 0.015 mmoles | HMPA 20 cc |

| | Composition | | Conversion | Tg |
|---|---|---|---|---|
| 27 | PS 65 % ES | 35 % | >90 % | −42° C; 200° C (Tf) |
| 28 | PS 70 % ACN | 30 % | >90 % | −39° C; 95° C |
| 29 | PS 90 % MACN | 10 % | >90 % | n.d. |
| 30 | PS 90 % PVL | 10 % | >90 % | −39° C; 172° C (Tf) |

Tg = glass transition temperature
Tf = melting temperature
PS = propylensulphide
ES = ethylensulphide
ACN = acrylonitrile
MACN = metacrylonitrile
PVL = pivalolactone In addition to the data shown in Table 3, the polymeric nature of the obtained products has been proved also with fractional extraction tests which exclude the presence of mechanical mixtures of two homopolymers.

We claim:

1. Polymerization catalyst constituted by the reaction product of a component which is a metal, metal hydride, metal alkyl or metal amide of a metal selected from the group consisting of the metals of groups IA, IIA and IIIA of the periodic system with a compound represented by the formula:

$$R-(X-(R')_m)_n-Y-R''$$

wherein X and Y, equal or different, are SO or $SO_2$; R and R'' are members of the group consisting of methyl, alkyl radicals containing from 2 to 10 carbon atoms, cycloalkyl, aryl, arylalkyl and alkyl cycloalkyl radicals; R' is a bivalent arylenic, cycloalkylenic, alkylarylenic, alkylcycloalkylenic radical or a methylenic chain having from 1 to 20 carbon atoms; $m$ is between 0 and 1; and $n$ is 1, 2 or 3; in the ratio of the component to the compound of between 10:1 and 0.3:1.

2. Process for the preparation of a polymerization catalyst wherein reaction is effected between a component which is a metal, metal hydride, metal alkyl or metal amide of a metal selected from the group consisting of the metals of groups IA, IIA and IIIA of the periodic system with a compound represented by the formula:

$$R-(X-(R')_m)_n-Y-R''$$

wherein X and Y, equal or different, are SO or $SO_2$: R and R'' are members of the group consisting of methyl, alkyl radicals containing from 2 to 10 carbon atoms, cycloalkyl, aryl, aryl-alkyl, and alkyl cycloalkyl radicals; R'' is a bivalent arylenic, cycloalkylenic, alkylarylenic, alkylcycloalkylenic radical or a methylenic chain having from 1 to 20 carbon atoms; $m$ is between 0 and 1; and $n$ is 1, 2 or 3; in the ratio of the component to the compound of between 10:1 and 0.3:1; in the temperature range between $-80°$ C and $+80°$ C.

3. Process for the preparation of polymerization catalysts according to claim 1, wherein the ratio of the component and the compound is 1:1.

4. Process for the preparation of polymerization catalysts according to claim 2, wherein the reaction is effected in the presence of a solvent chosen from the group consisting of hydrocarbons, aromatic hydrocarbons, tetrahydrofuran, dioxane, hexamethylphosphoramide and liquid ammonia.

* * * * *